(12) United States Patent
Roman

(10) Patent No.: US 7,339,673 B2
(45) Date of Patent: Mar. 4, 2008

(54) MINIATURE OPTICAL READHEAD FOR OPTICAL DIAGNOSTIC DEVICE

(75) Inventor: Juan F. Roman, Suffolk (GB)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 265 days.

(21) Appl. No.: 11/158,634

(22) Filed: Jun. 22, 2005

(65) Prior Publication Data
US 2005/0237531 A1 Oct. 27, 2005

Related U.S. Application Data

(63) Continuation-in-part of application No. PCT/US05/07227, filed on Mar. 3, 2005.

(60) Provisional application No. 60/550,811, filed on Mar. 5, 2004.

(51) Int. Cl.
*G01J 3/50* (2006.01)

(52) U.S. Cl. .................. 356/402; 356/406; 356/425; 356/446; 422/82.05

(58) Field of Classification Search ............... 356/420, 356/402, 407, 408, 421, 425, 39; 422/56, 422/57, 58, 59, 82.05
See application file for complete search history.

(56) References Cited

U.S. PATENT DOCUMENTS 4,755,058 A 7/1988 Shaffer
5,374,395 A * 12/1994 Robinson et al. ............. 422/64
5,408,535 A 4/1995 Howard, III et al.
5,724,148 A * 3/1998 Howard et al. ............. 356/425
6,055,060 A 4/2000 Bolduan et al.
2007/0064220 A1* 3/2007 Stock et al. .................. 356/73

FOREIGN PATENT DOCUMENTS

EP 0 560 410 B1 10/2002

OTHER PUBLICATIONS

Clear Blue (tm) pregnancy test reader: http://www.unipath.com/clearbluedigital.cfm.

* cited by examiner

Primary Examiner—F. L. Evans
Assistant Examiner—Abdullahi Nur
(74) Attorney, Agent, or Firm—Noam Pollack

(57) ABSTRACT

A miniature readhead for a photometric diagnostic instrument includes a housing of hand-held form factor, configured for receiving reagent sample media therein. The sample media has a plurality of test areas configured to react with, and change color, according to an amount of an analyte in a sample. The holder is sized and shaped for forming an indexed fit with the sample media and includes an array of light sources coupled to the housing, each of the light sources configured to emit light onto a respective one of the test areas. An array of chambers respectively containing an array of light detectors, is configured to enable each of the light detectors to receive diffuse, non-specular reflections of the light from the test areas, while substantially preventing the light detectors from receiving specular reflections of the light.

35 Claims, 6 Drawing Sheets

MINIATURE OPTICAL READHEAD FOR OPTICAL DIAGNOSTIC DEVICE

RELATED APPLICATIONS

This application is a Continuation-In-Part of co-pending P.C.T. Patent Application No. US05/07227, designating the United States, entitled Handheld Optical Diagnostic Device Having Image System Array, filed Mar. 3, 2005, which claims priority to U.S. Provisional Patent Application Ser. No. 60/550,811, entitled Handheld Optical Diagnostic Device Having Image System Array, filed on Mar. 5, 2004.

BACKGROUND

1. Technical Field

The present invention generally relates to the field of clinical chemistry. More particularly, the present invention relates to a readhead for an optical diagnostic system that analyzes the color change associated with one or more test areas on sample media following contact thereof with a liquid specimen, such as urine or blood.

2. Background Information

Throughout this application, various patents are referred to by an identifying citation. The disclosures of the patents referenced in this application are hereby incorporated by reference into the present disclosure.

Sample media such as reagent test strips are widely used in the field of clinical chemistry. A test strip usually has one or more test areas spaced along the length thereof, with each test area being capable of undergoing a color change in response to contact with a liquid specimen. The liquid specimen usually contains one or more constituents or properties of interest. The presence and concentrations of these constituents or properties are determinable by an analysis of the color changes undergone by the test strip. Usually, this analysis involves a color comparison between the test area or test pad and a color standard or scale. In this way, reagent test strips assist physicians in diagnosing the existence of diseases and other health problems.

Color comparisons made with the naked eye can lead to imprecise measurement. Today, strip reading instruments exist that employ reflectance photometry for reading test strip color changes. These instruments accurately determine the color change of a test strip within a particular wavelength range or bandwidth. Examples of such instruments include those sold under the CLINITEK® trademark by Bayer Healthcare Diagnostics Division of Bayer HealthCare LLC (Norwood, Mass.) and/or as disclosed in U.S. Pat. Nos. 5,408,535 and 5,877,863 (the '863 patent), both of which are fully incorporated by reference herein. These instruments are typically used to detect colors associated with a urine specimen on a MULTISTIX® (Bayer) reagent strip.

Another strip reading instrument utilizing reflectance photometry to read multiple test strips is disclosed in U.S. Pat. No. 5,055,261. An operator sequentially places test strips in a loading area. An arm orients the test strips on rails extending from the loading area to one or more reading stations employing readheads.

A common aspect of these instruments is that their relative size and complexity, particularly with respect to those utilizing automated test pad transport systems, render them relatively bulky and difficult to transport. Rather, these devices tend to be installed at a dedicated testing center or laboratory, where samples are aggregated and tested in bulk. Unfortunately, such aggregation of samples from multiple patients presents opportunities for error due to mislabeling of the samples and/or the test results. Moreover, in many instances, the time required for transporting the samples to and from the processing center, and for testing and recording the results, may be problematic.

A portable diagnostic device is described in U.S. Provisional Patent Application Ser. No. 60/550,811, entitled Handheld Optical Diagnostic Device Having Image System Array, filed Mar. 5, 2004, which is fully incorporated herein by reference. This device advantageously provides a portable means for analyzing the aforementioned reagent strips. This device, however, relies on relatively complex imaging technology.

Other portable diagnostic devices include the Clearblue™ Digital Pregnancy Test device (Unipath Limited, UK) and the glucose test system disclosed in U.S. Pat. No. 6,055,060. These are generally single test devices, i.e., used to test for single analytes, such as the hCG hormone (pregnancy) or glucose. As such, these devices may be optimized for relatively narrow spectral (color) detection ranges, such as blue in the case of the Clearblue™ tester, and yellow/green for the glucose test system. Moreover, even with the relative simplicities inherent with such single analyte testing environments, these devices tend to utilize relatively complex readhead systems that may be labor intensive to manufacture.

A need therefore exists for an inexpensive, portable diagnostic testing device that enables a care provider to obtain quick and accurate test results for a range of analytes without the need for sending sample media to a remote testing center for processing. A need also exists for an inexpensive, portable diagnostic testing device, that enables quick and accurate test results without the need to engage in relatively complex image capture and analysis techniques. A need also exists for a relatively simple and easily manufactured readhead for a portable diagnostic testing device.

SUMMARY

An aspect of the present invention includes a miniature readhead for a photometric diagnostic instrument, for illuminating a target area and detecting color information from the target area. The readhead includes a housing having a hand-held form factor including a holder configured for receiving reagent sample media therein, the sample media having a plurality of test areas disposed in spaced relation thereon, each of the test areas configured to react with a sample when disposed in contact with the sample and to change color according to an amount of an analyte in the sample. The holder is sized and shaped for forming an indexed fit with the sample media and includes an array of light sources coupled to the housing, each of the light sources configured to emit light onto a respective one of the test areas. An array of chambers are located in the housing, and an array of light detectors are respectively disposed within the array of chambers. The chambers are configured to enable each of the light detectors to receive diffuse, non-specular reflections of the light from a respective one of the test areas when the sample media is indexed within the holder. The chambers are configured to substantially prevent the light detectors from receiving specular reflections of the light.

Another aspect of the invention includes a miniature photometric diagnostic instrument including a housing having a hand-held form factor. The housing includes a holder configured for receiving reagent sample media therein, the sample media having a plurality of test areas disposed in spaced relation thereon, each of the test areas configured to react with a sample when disposed in contact with the sample and to change color according to an amount of an analyte in the sample. The holder is sized and shaped for forming an indexed fit with the sample media. An array of light sources are coupled to the housing, each of the light sources configured to emit light onto a respective one of the test areas. An array of chambers are located in the housing, and an array of light or color detectors are respectively disposed within the array of chambers. The chambers are configured to enable each of the light or color detectors to receive non-specular reflections of the light from a respective one of the test areas when the sample media is indexed within the holder, while substantially preventing the light or color detectors from receiving specular reflections of the light. A processor is operatively coupled to the light or color detectors and to the light sources, and is configured to analyze the reflections received by the light or color detectors. The processor is also configured to derive a diagnosis value from the analysis, and to generate an output corresponding thereto.

A further aspect of the invention includes a method for reading reagent sample media, the sample media having a plurality of test areas disposed in spaced relation thereon, each of the test areas configured to react with a sample when disposed in contact with the sample and to change color according to an amount of an analyte in the sample. The method includes receiving the sample media into a sample holder of a readhead of a photometric diagnostic device, the readhead having a hand-held form factor, and the sample holder configured to maintain the sample media in an indexed fit therewith. Light is sequentially emitted onto a respective one of the test areas, and diffuse, non-specular reflectances of the test areas are sequentially captured with respective ones of an array of light or color detectors. Specular reflections of the light are prevented from reaching the array of light or color detectors. The color of the non-specular reflectances is determined, to derive the amount of constituent or property in the sample. An output signal is then generated, which corresponds to the amount of the constituent or property.

BRIEF DESCRIPTION OF THE DRAWINGS

The above and other features and advantages of this invention will be more readily apparent from a reading of the following detailed description of various aspects of the invention taken in conjunction with the accompanying drawings, in which.

DETAILED DESCRIPTION

Figure 1:
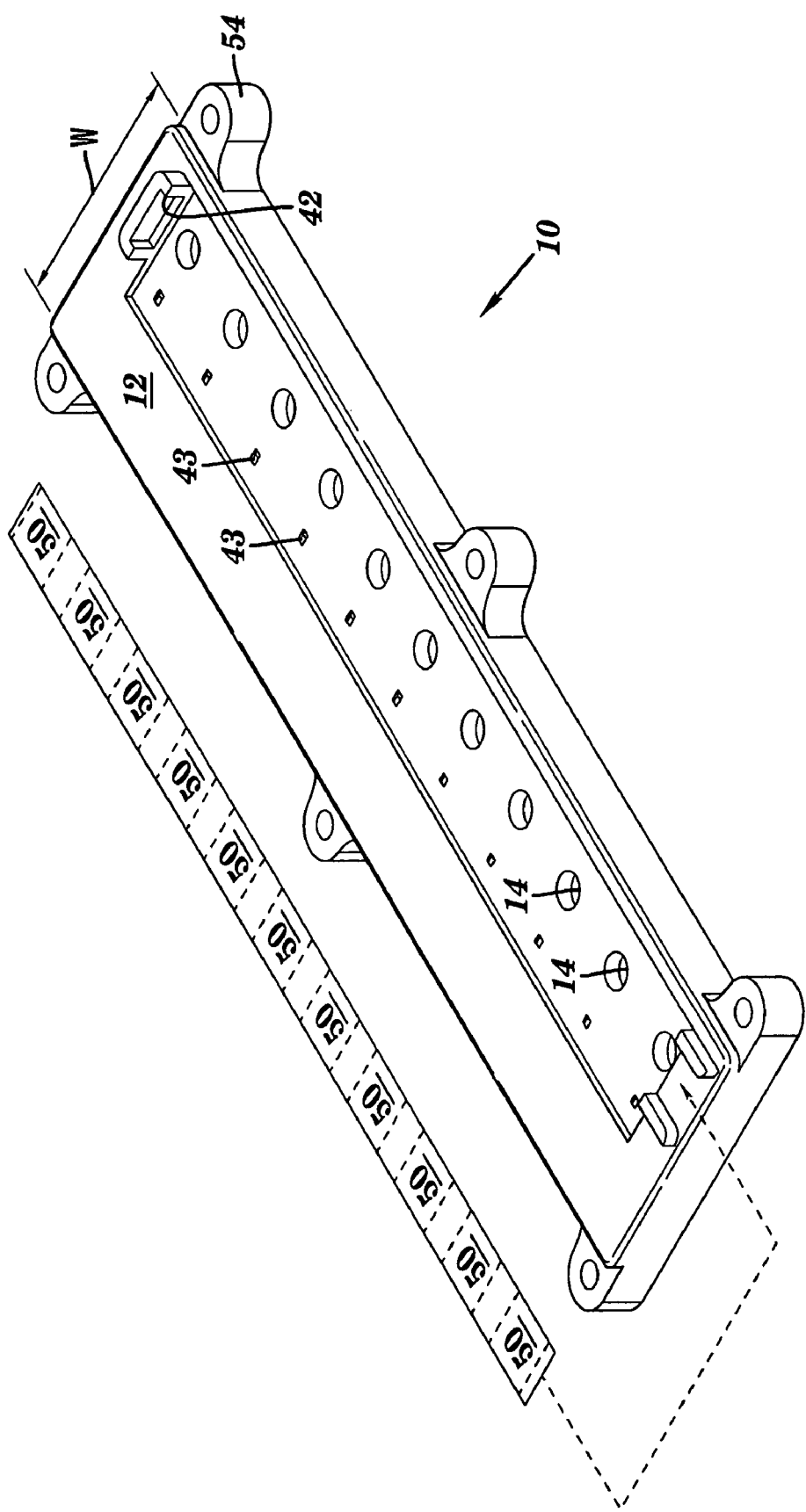
FIG. 1 is an elevational, partially exploded view of a readhead of the present invention, along with a sample media strip.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals.

Figure 2:
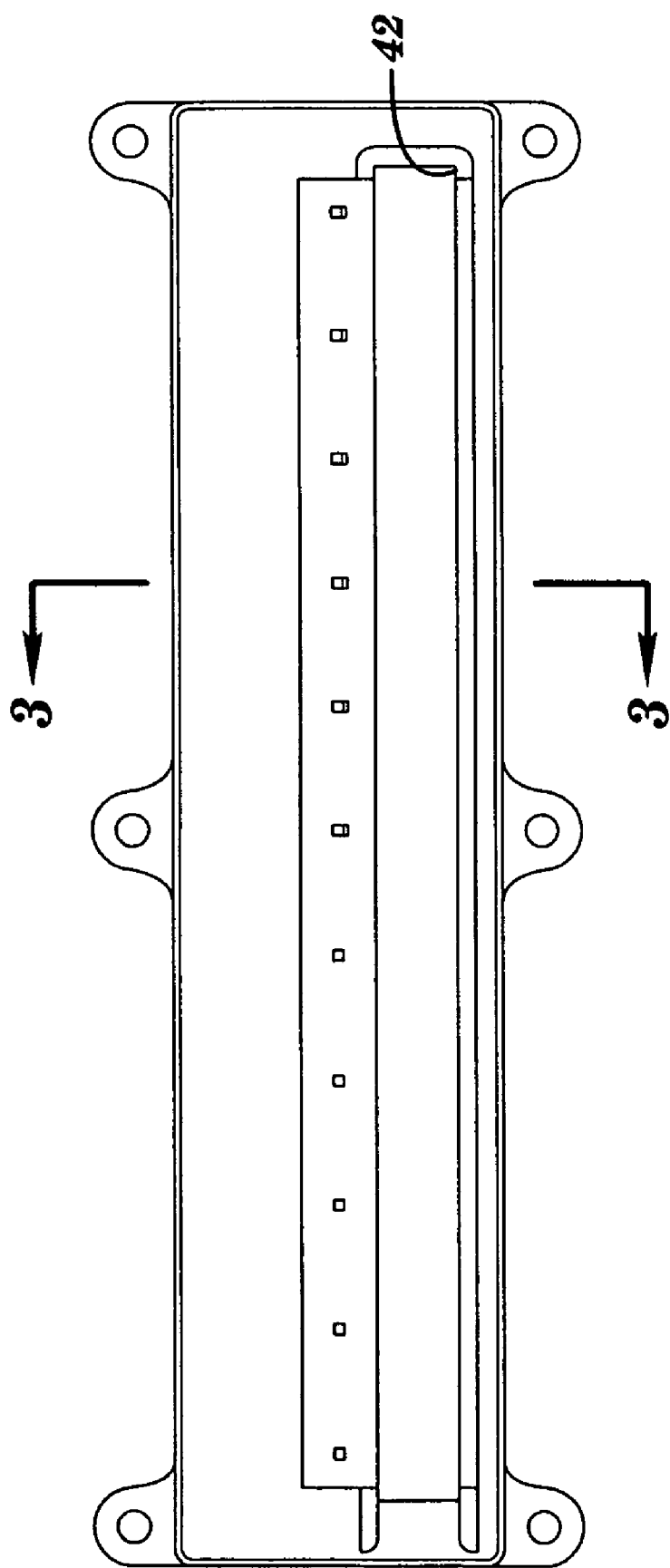
FIG. 2 is a view similar to that of FIG. 1, with the sample media strip in operative engagement with the readhead.
Figure 3:
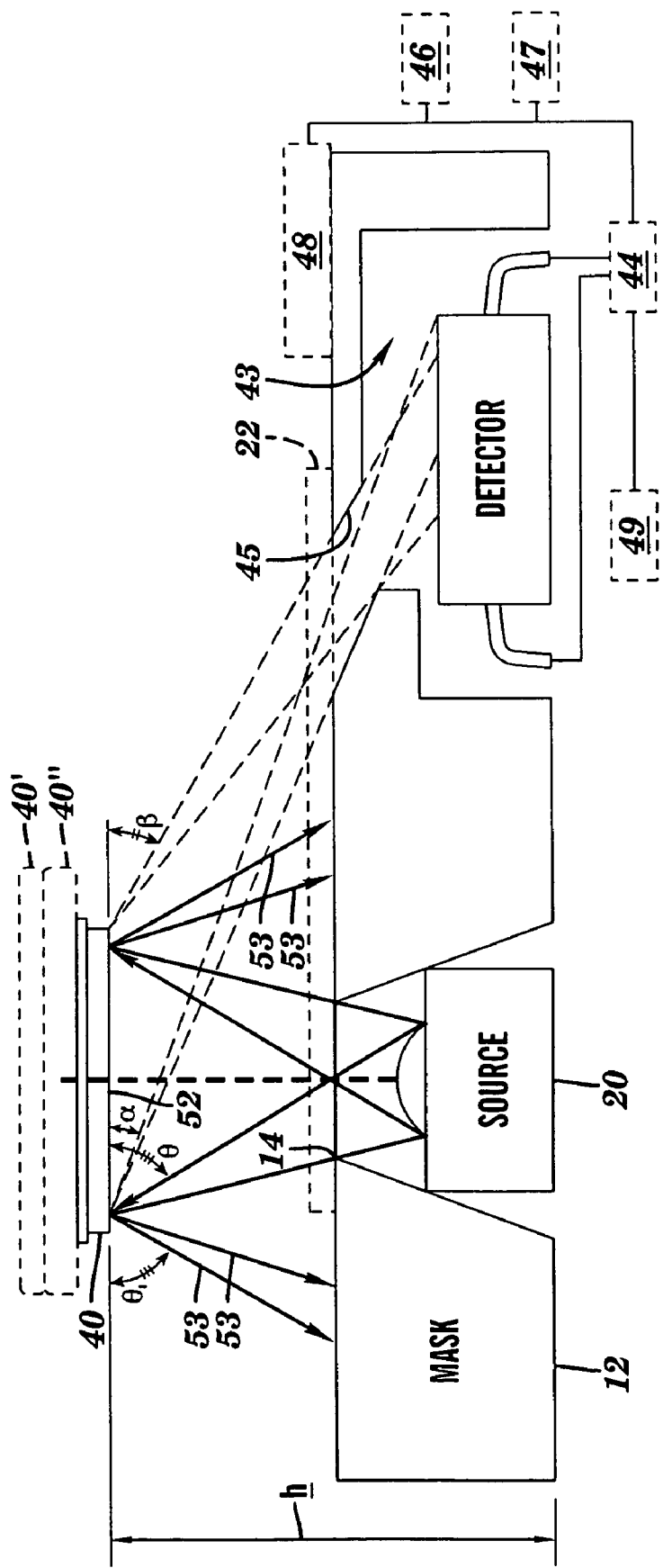
FIG. 3 is a cross-sectional, schematic view, on an enlarged scale, taken along 3-3 of FIG. 2, showing a field of view of an exemplary detector, and having aspects of an alternate embodiment shown in phantom.

An overview of an embodiment of the invention is provided with reference to FIGS. 1-3. This embodiment includes a readhead 10 for a photometric diagnostic instrument of the type used to analyze reagent sample media, such as the above-referenced MULTISTIX® (Bayer) test strip. Readhead 10 includes a geometrical arrangement of light detectors or color detection means and light sources that provides a particularly small form factor, suitable for handheld, battery powered operation. This embodiment also advantageously uses relatively inexpensive components, relying on diffuse reflectance color detection rather than imaging technology. Moreover, this color detection approach simplifies processing to advantageously reduce processing overhead, while providing high reliability.

In this embodiment, readhead 10 includes an array of light sources 20 pitched to match that of the test areas (e.g., pads) 50 of the sample media (e.g., test strip) 40. The array of light sources is superposed with a sample holder 42 sized and shaped for forming an indexed fit with the sample media 40. An optical or mechanical sensor may be used to check that the indexation is correct, e.g., to ensure that the strip has been fully inserted. An array of light or color detectors 70 is also disposed within readhead 10 to respectively detect diffuse reflections from each of the test areas 50 when the sample media is indexed within holder 42. Each of the detectors 70 is placed within its own chamber 43 which enables it to receive light from its respective test area 50, while nominally preventing it from receiving stray reflectances from other test areas to eliminate cross-talk. In addition, each detector 70 and cavity 43 is configured, e.g., by appropriately sizing and shaping the cavity, to prevent interference by specular reflections from sample media 40.

In particular embodiments, a processor 44 is coupled to the detectors to analyze the captured reflectances (colors) to derive a diagnosis value from the analysis, and generate an output corresponding thereto. The output may be fed to a port 46, e.g., for remote display, and/or displayed on an integral display 48.

As is familiar to those skilled in the art, sample media 40 may include typical urine analysis strips, having paper pads disposed in spaced relation thereon, which are soaked in chemical reagents that react with a specimen sample to change color according to the medical condition of the patient, i.e., according to levels of various analytes in the sample. As used herein, the term 'analyte' refers to a constituent, or to a property (e.g., pH) of the sample. Examples of such media 40 include the aforementioned MULTISTIX® test strips. Alternatively, sample media 40 may include a conventional immuno-assay cassette, e.g., the CLINITEST® hCG cassette (Bayer), (such as shown schematically in phantom as 40' in FIG. 3), having an area soaked in chemical reagents that react to the sample to reveal a colored line or pattern of lines according to the medical condition of the patient.

Other suitable sample media may include conventional microfluidic devices (such as shown schematically as 40" in FIG. 3) which typically include a substrate having a series of narrow channels, e.g. on the order of microns in width, through which a fluid such as blood or urine may travel. The channels conduct the fluid to various test areas on the device. These devices enable various tests to be performed using only a small amount of fluid, e.g., using a small drop of liquid. Exemplary microfluidic devices are described in U.S. patent application Ser. No. 10/082,415 filed on Feb. 26, 2002 and entitled Method and Apparatus For Precise Transfer And Manipulation of Fluids by Centrifugal and or Capillary Forces.

For convenience and clarity, various embodiments of the present invention are described as using sample media 40 in the form of MULTISTIX® test strips, with the understanding that substantially any form of sample media may be used without departing from the spirit and scope of the present invention. Embodiments of the present invention may be particularly beneficial when used with alternate media such as immuno-assay cassettes due to their often faint or otherwise difficult to read results.

Software associated with the various embodiments of the present invention can be written in any suitable language, such as C++; Visual Basic; Java; VBScript; Jscript; BCMAscript; DHTM1; XML and CGI. Any suitable database technology may be employed, including but not limited to versions of Microsoft Access and IMB AS 400.

Particular embodiments of the present invention will now be described in detail. Turning to FIGS. 1-3, in embodiments of the present invention, a readhead 10 includes a housing 12 conveniently formed as a unitary molded (e.g., injection olded) component. An elongated recess sized and shaped to receive and form an indexed fit with test strip 40 is molded into the housing to form holder 42.

In the embodiment shown, sample media 40 includes a reagent strip having a predetermined number of test areas (e.g., reagent pads) 50 thereon. Each reagent pad 50 includes a relatively absorbent material impregnated with a respective reagent, each reagent and reagent pad 50 being associated with a particular test to be performed. When urinalysis tests are performed, they may include, for example, a test for leukocytes in the urine, a test of the pH of the urine, a test for blood in the urine, etc. When each reagent pad 50 comes into contact with a urine sample, the pad changes color, depending on the reagent used and the characteristics of the sample. As discussed above, reagent strip 40 may be a MULTISTIX® reagent strip commercially available from Bayer Corporation. The sample media may alternatively include an immuno-assay cassette 40' or a microfluidic device 40" as shown in phantom.

An array of apertures 14 are spaced within sample holder 42 at a pitch (spacing) which corresponds to that of the test areas (pads) 50 of test strip 40. An array of light sources 20 are similarly spaced within housing 12, to emit light through apertures 14 onto a respective ones of the test areas 50 when the sample media 40 is indexed within holder 42. Light sources 20 may include substantially any light emitting or coupling device, such as light emitting diodes (LEDs), VCSELs, incandescent lamps (e.g., tungsten), laser emitting devices, such as solid state lasers etc., lightguides, organic LEDs, diode lasers, optical fibers, and/or nominally any other light sources that may be developed in the future. Alternatively, it may even be possible for particular embodiments of the present invention to simply utilize ambient light (e.g., sunlight), e.g., with appropriate light filtering.

In particular embodiments, each light source 20 includes an integrated LED package of two or more LEDs of distinct colors. For example, as shown, source 20 includes an RGB package of integrated red, green and blue LEDs.

The LEDs 20 are configured to operate in a conventional manner, as discussed hereinbelow, e.g., by selectively emitting monochromatic radiation of mutually distinct wavelengths, such as corresponding to red light, green light and blue light. Alternatively, the RGB LEDs may be operated simultaneously to approximate full spectrum, white light.

A transparent or translucent cover 22, such as fabricated from glass or plastic, may be optionally superposed with apertures 14 and with channels formed by shielding 45 of chambers 43 to help prevent dirt and debris from entering and obscuring light sources 20 or detectors 70.

Housing 12 also includes an array of chambers 43 spaced to receive light reflected from respective test pads 50, for capture by detectors 70 (FIG. 3) disposed therein. Although alternate spacing may be used, in the embodiment shown, chambers 43 are provided with spacing similar to that of test pads 50 and light sources 20.

Chambers 43 are each configured with shielding 45 (FIG. 3) which defines a channel aimed at a respective test pad 50. These channels effectively serve as partitions between adjacent chambers, to substantially prevent light from other test pads 50 from entering the chamber. Moreover, as best shown in FIG. 3, the positioning of chambers 43, including the angle at which the channel is aimed, in combination with the size of aperture 14, is configured to substantially prevent specular reflections of source 20 from being captured by detectors 70.

It should be recognized that the size of various individual components, such as the individual apertures 14 and the channels formed by shielding 45, may be distinct from one another. Such distinct sizing enables the amount of illumination and/or reflection associated with a particular test pad/reagent to be conveniently optimized. In this regard, pads containing particular reagents are often disposed on the same position on the strip (e.g. pads containing leucocytes are often placed on the first pad position), and may require more or less illumination than test pads at other locations on the strip.

In the embodiment shown, this is accomplished by disposing chambers 43 (and aiming the channels defined by shielding 45) so that the magnitude of angles of reflectance $\alpha$, $\beta$, etc., of light received by detectors 70, is dissimilar from that of the angles of incidence $\theta$ relative to reflecting surfaces 52 of test strip 40.

For example, in the embodiment shown in FIG. 3, light sources 20 are disposed to emit light at an angle of incidence $\theta$ of approximately 60 to 90 degrees relative to the substantially planar reflecting surface 52 of strip 40. Chambers 43 and detectors 70, however, are offset, e.g., in the planar direction, from strip 40 (and from sources 20), so that they receive only diffuse or scattered reflections emanating at angles of reflectance $\alpha$, $\beta$. In some particular exemplary embodiments, the magnitudes of these angles of reflectance may differ by 25 percent or more from those of the angles of incidence. Moreover, in the example shown, the positioning of chambers 43, including the angle at which the channel is aimed, in combination with the size of aperture 14, is configured so that the specular reflected rays 53 land on the housing 12 at least one mm away from the edge of the channel.

One skilled in the art will recognize that specular reflections (shown at 53 in FIG. 3) are generated, e.g., from wet surfaces, along angles reflectance $\theta_1$ that are equal in magnitude to the angles of incidence $\theta$ of light thereon. Thus, the use of dissimilar angles as described, i.e., viewing the test strip 40 from a shallow angle relative to the angle of incidence, helps ensure that specular reflections (such as from excess liquid on the strip), are not received by detector(s) 70. These shallow reflectance angles also provide for the elimination of specular reflections without complicated housing geometries configured to attenuate undesired reflections. This elimination of specular reflection prior, rather than after detection, advantageously eliminates substantial complexity and potential errors otherwise associated with attempting to eliminate or compensate for specular reflections during processing. This construction thus provides for relatively simplified processing, for improved detection simplicity and efficiency.

Although the embodiments shown and described herein include angles of reflectance that are less than angles of incidence, those skilled in the art should recognize that the angles of reflectance may be greater than the angles of incidence, without departing from the spirit and scope of the present invention.

Those skilled in the art should also recognize that the relative positions of the light sources 20 and detectors 70 may be reversed relative to those shown in FIG. 3. For example, light sources 20 may be offset in the planar direction relative to pads 50, while detectors 70 may be aligned with the pads in the planar direction, without departing from the spirit and scope of the present invention.

Figure 4:
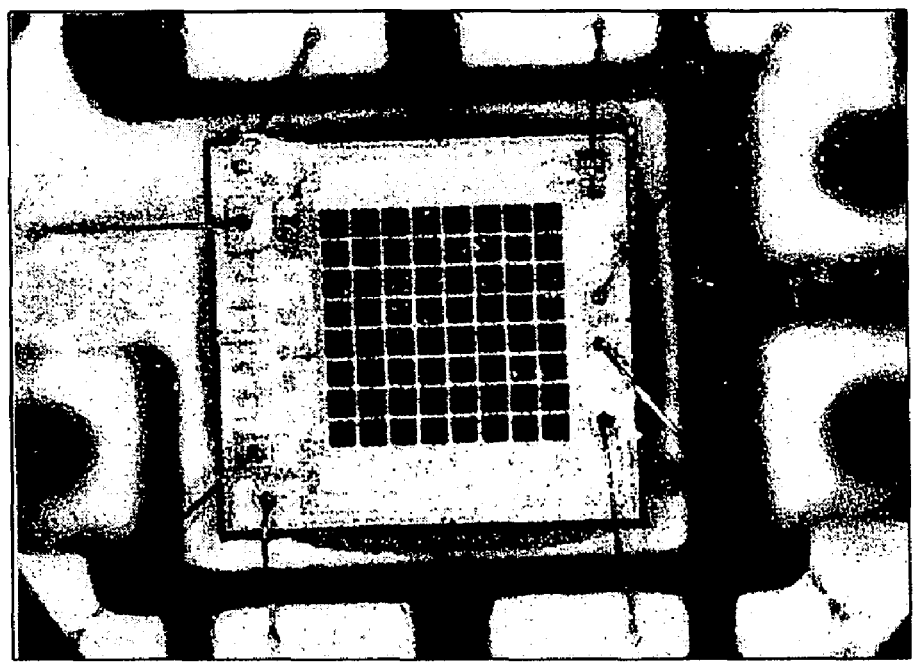
FIG. 4 is an elevational view, on an enlarged scale, of an exemplary detector used in the embodiments of FIGS. 1-3.

Turning now to FIG. 4, detector 70 may include nominally any conventional light detector, either with or without color filters. In one exemplary embodiment, detector 70 may include a TCS230 detector commercially available from TAOS, Inc. The TCS230 device includes filters of three colors (RGB) superposed with an array of individual light sensors. In this embodiment, the RGB LEDs of each light source 20 may be operated simultaneously to illuminate a test area with approximately full spectrum, white light, as discussed hereinabove. The TCS230 generates a digital output, via an integral analog-to-digital converter, to obviate any need for subsequent signal conversion. This device is also relatively compact, having an active area of 1.15×1.15 mm.

Alternatively, a light detector without color filters, such as an array of CMOS sensors similar to those of the TCS230 device, but without filters, may be used. In such an embodiment, the test areas may be sequentially illuminated with monochromatic light, such as by individual actuation of the red, green and blue LEDs of each light source 20 as discussed above.

As a further alternative, a light detector having color filters may be illuminated monochromatically. For example, a detector 70, such as the TCS230, may be operated in conjunction with sequential illumination by the red, green and blue LEDs of light source 20, to provide enhanced color detection and filtering.

In accordance with the foregoing, embodiments of readhead 10 may be provided with a relatively small form factor, similar in length to that of a MULTISTIX® test strip 40 as shown in FIG. 1, i.e., approximately 82 mm. The use of the aforementioned shallow angles of reflectance also enables the detectors 70 to be disposed in the same plane as light sources 20. This lateral placement of detectors 70 relative to the light sources 20 thus enables test strip 40 to be disposed relatively closely to light sources 20 for a particularly compact configuration. In this regard, embodiments of readhead 10 have advantageously been provided with a low profile, including a height h of only 6 mm, and a width w of only 12 mm.

Accordingly, this readhead 10 may be easily incorporated into a variety of photometric diagnostic instruments, such as a CLINITEK® instrument. In such a configuration, readhead 10 may be electrically coupled to the instrument, which would supply power and operate the readhead 12 in a conventional manner, as will be described hereinbelow. Moreover, various modifications may be made to the particular configuration of housing 12, such as, for example, the provision of feet 54, to facilitate such integration into the diagnostic instrument.

Alternatively, readhead 10 may be provided with additional components, as shown in phantom in FIG. 3, including for example, one or more of a processor 44, memory 47, an output port 46, integral display 48, and a power supply (e.g., battery) 49. These additional components 44, 46, 48, 49 may be integrated into housing 12, to form a unitary handheld photometric diagnostic instrument. Alternatively, one or more of these components may be associated with other devices (e.g., a CLINITEK® instrument), which may be communicably coupled, such as via a network, thereto.

In operation, light sources (e.g., LEDs) 20 are actuated, typically one at a time to illuminate reagent strip 40. Detector 70 then receives enough reflected light from the reagent strip 40 to determine the color thereof. Each individual detector 70 senses light from a particular location on reagent media 40, 40', 40". Alternatively, in some embodiments, all of the LEDs 20 may be illuminated at once, and all of the detectors 70 actuated simultaneously to detect the colors of light reflected from all of the reagent test areas (e.g., pads) 50.

For example, referring to Table I, a conventional or simplified operating system (OS) of the CLINITEK® instrument running in the host instrument or in processor 44, may actuate LED 20 at 80 to illuminate media 40, 40', 40". Detector 70 may also be actuated 82 to detect the color of light reflected from the media, and optionally store 84 the color information to memory 47. The OS may actuate 86 the processor in a conventional manner to analyze the color information, such as by comparing the captured color information to a database of known color-coded diagnostic values. Steps 80-86 may be repeated for additional test areas (pads).

TABLE I

| | |
|---|---|
| 80 | Actuate light source |
| 82 | Detect color of reflected light |
| 84 | Optionally store the color information to memory |
| 86 | Analyze color information |
| 88 | Repeat steps 80-86 for additional test areas |

Additional operational aspects are substantially similar to those of conventional photometric diagnostic instruments such as the above-referenced CLINITEK® instrument, and/or as described in the above referenced U.S. Provisional Patent Application Ser. No. 60/550,811. Such operational aspects are briefly described with respect to FIGS. 5 & 6.

Figure 5:
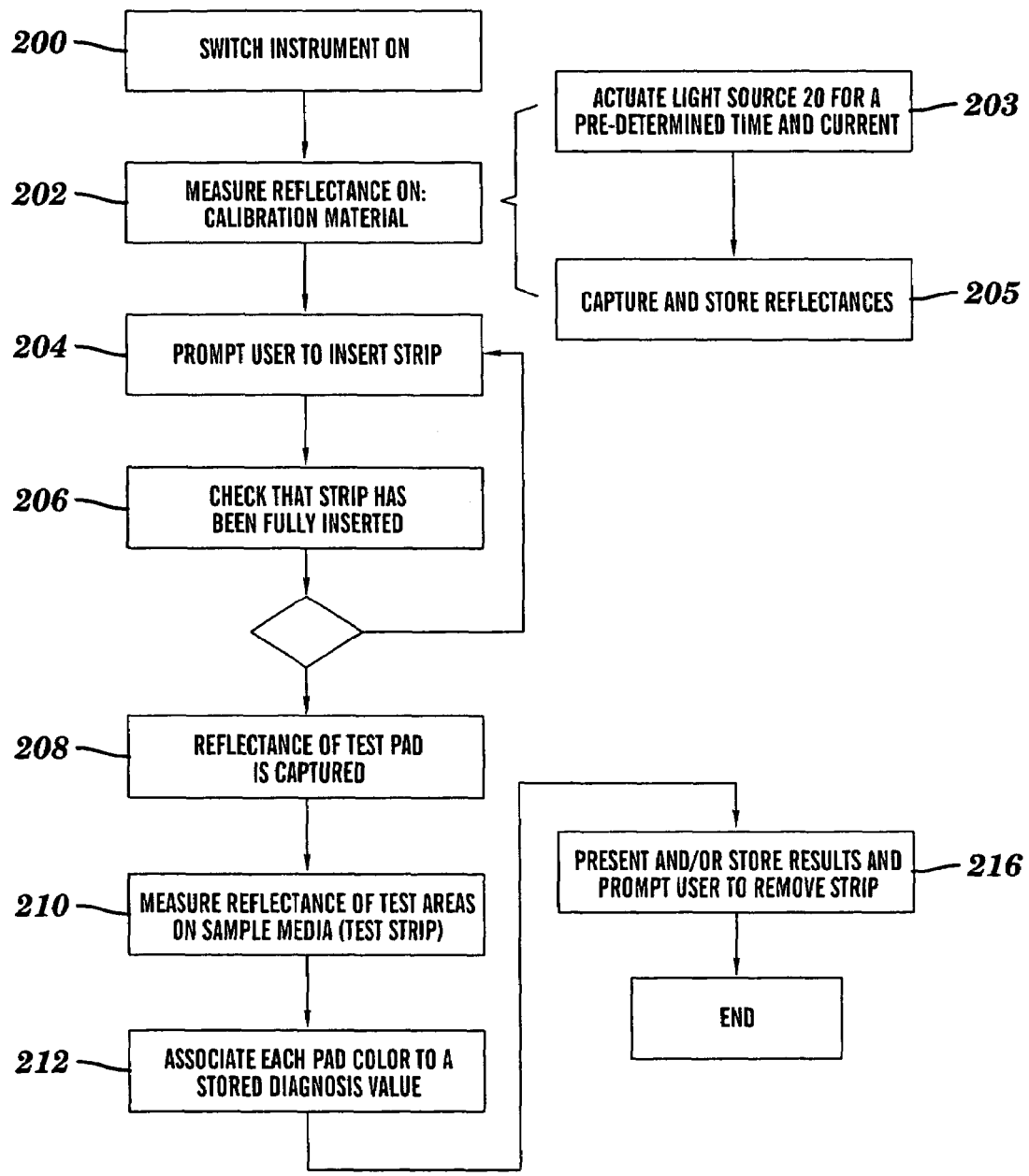
FIG. 5 is a flow chart of operational aspects of embodiments of the present invention.

Turning to FIG. 5, the instrument, including readhead 10 is initially powered up at 200, after which reflectance of calibration material is measured at 202. Calibration 202 may be effected automatically, e.g., each time the instrument is powered up 200, or may be initiated by the user who inserts a calibration material, for example, in response to an audible or visual prompt.

Calibration 202 includes actuating or otherwise exposing the calibration material to light source(s) 20 for a pre-determined time and pre-determined current (e.g., when using an electrically actuated source 20) at 203, and capturing and storing reflectances of the calibration material (e.g., per Table I above) at 205. These calibration reflectances are used to effect sample measurement 210 as discussed in detail below with respect to FIG. 6.

Once calibration is complete, the instrument may prompt the user to insert sample media 40, 40', 40" at step 204. Upon insertion, at 206, the system checks for an appropriate signal, e.g., from one or more of detectors 70, (or alternatively from nominally any other electromechanical switch or actuator) indicating that sample 40 has been fully inserted. If this signal has not been received, then the system loops back to step 204 to re-prompt the user to fully insert the sample. If the signal was received, then reflectance is captured 208 and measured 210 (described in greater detail below with respect to FIG. 6), and compared to calibration values generated during calibration 202.

At 212, these reflectance values (colors) are compared to known diagnosis values stored in memory (e.g., 47). At 216, results (i.e., diagnosis values) generated by step 212 are then outputted to a display (e.g., 48) and/or stored to memory, and the user prompted to remove the strip.

Figure 6:
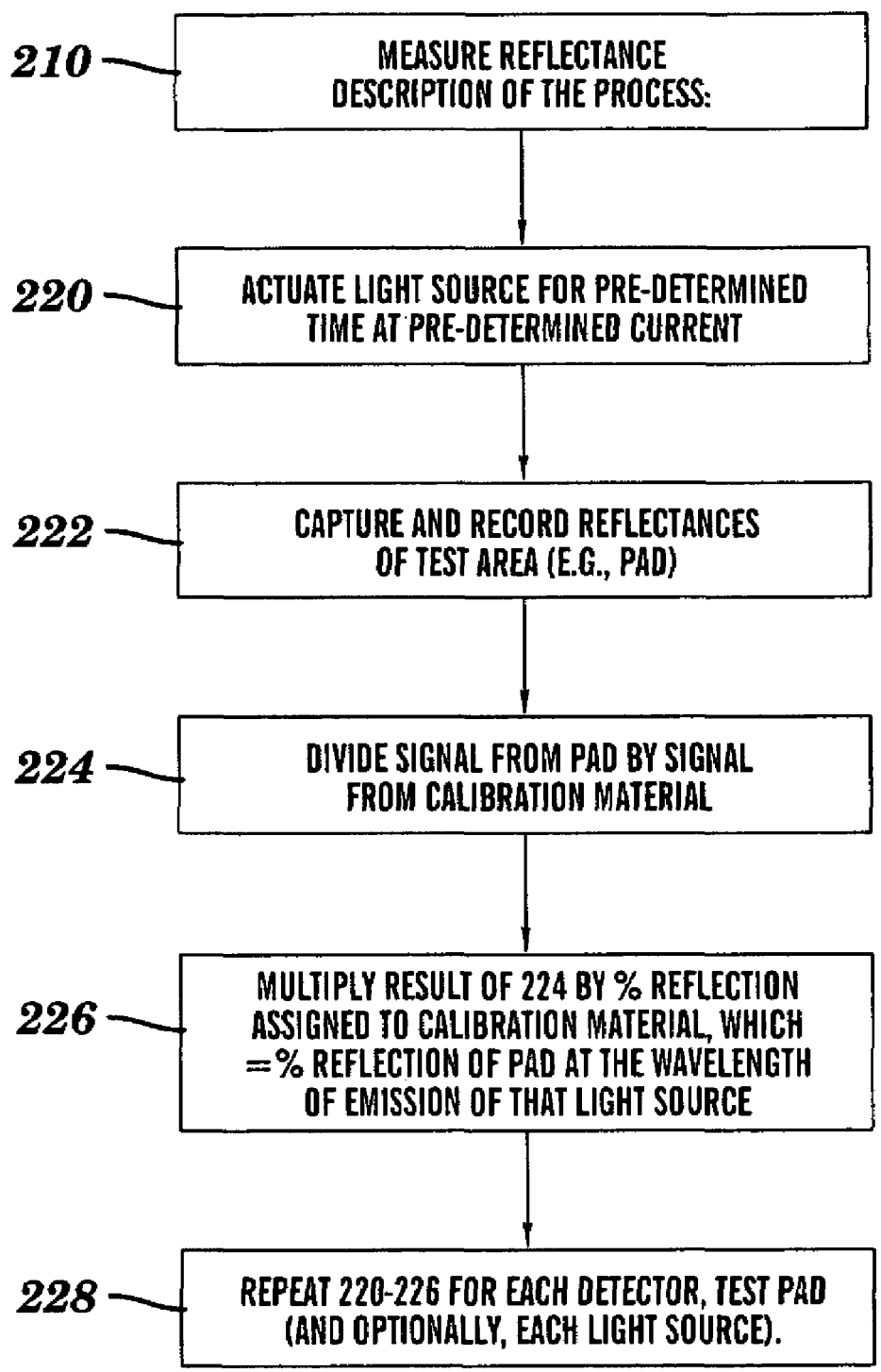
FIG. 6 is a flow chart of measurement steps effected during the operation of FIG. 5.

Turning now to FIG. 6, measurement 210 is discussed in greater detail. As shown, this measurement includes actuating light source 20 for a pre-determined time and pre-determined current (e.g., for electrically actuated light sources) at 220. This pre-determined time and current is preferably the same as that used during steps 203 and 205 of the calibration discussed above. The steps of Table I are effected relative to sample media 40, 40', 40" etc., and signals received (i.e., reflectances captured) by detectors 70 are saved to memory at 222. At 224, a numerical value of the captured reflectance is divided by a numerical equivalent of the reflectance value of the calibration material acquired at step 205 above. At 226, the result of 224 is multiplied by the known percent reflection of the calibration material to generate the percent reflection of the particular pad or portion of sample 40, etc., at the known wavelength of emission of the particular light source 20. This percent reflection, used alone or in combination with additional percent reflectances determined using light sources of various discrete wavelengths as discussed below, corresponds to a color that may be correlated to known diagnosis values as discussed above.

As shown at 228, steps 220-226 may be repeated for each portion of interest of the sample media (e.g., each test pad and each detector), and optionally, for each light source, in the event light sources of distinct wavelengths (e.g., colors) are used individually. In this regard, the individual red, green and blue LEDs of each LED package 20 may be actuated simultaneously for an approximation of full spectrum white light as mentioned above. Alternatively, the RGB LEDs may be actuated individually to obtain percent reflectances at multiple discrete wavelengths. Percent reflectances may be obtained at any, or each, of the three wavelengths (e.g. RGB). In many instances, it may be desirable to use individual percent reflectances obtained using all three wavelengths to infer the color of the pad. In other instances, such as when it is expected that a reflectance will be within a particular range (e.g., blue-green), the actual color may be inferred using fewer (e.g., two, or even one) discrete wavelengths.

The following illustrative example is intended to demonstrate certain aspects of the present invention. It is to be understood that this example should not be construed as limiting.

EXAMPLE

A readhead 10 was fabricated substantially as shown and described hereinabove with respect to FIGS. 1-4. Housing 12 was injection molded with dimensions of 5×12×82 mm, with a sample holder 42 configured to receive a MULTISTIX® (Bayer) test strip 40. Housing 12 was fitted with an array of eleven RGB LEDs 20. An array of eleven chambers 43 were fabricated with shielding 45 substantially as shown and described. A TCS230 (TAOS, Inc.) pixilated color detector having an active area of 1.15×1.15 mm, was installed within each chamber 43. The LEDs 20 were disposed to provide illumination at an angle of incidence of approximately 90 degrees relative to a test strip 40 disposed within holder 42. Chambers 43 and color detectors 70 were configured to receive reflected light at angles of reflectance between approximately 10 and 30 degrees relative to strip 40. This readhead was tested and found to successfully generate similar performance to that of conventional instruments of larger form factors (i.e., CLINITEK® STATUS, CLINITEK® 50 and CLINITEK® 500).

In the preceding specification, the invention has been described with reference to specific exemplary embodiments thereof. It will be evident that various modifications and changes may be made thereunto without departing from the broader spirit and scope of the invention as set forth in the claims that follow. The specification and drawings are accordingly to be regarded in an illustrative rather than restrictive sense.

Having thus described the invention, what is claimed is:

1. A miniature readhead for a photometric diagnostic instrument for illuminating a target area and detecting color information from the target area, the readhead comprising:
    a housing having a hand-held form factor including a holder configured for receiving reagent sample media therein, the sample media having a plurality of test areas disposed in spaced relation thereon, each of the test areas configured to react with a sample when disposed in contact with the sample and to change color according to an amount of an analyte in the sample;
    the holder sized and shaped for forming an indexed fit with the sample media;
    an array of light sources coupled to said housing, each of said light sources configured to emit light onto a respective one of the test areas;
    an array of chambers disposed in said housing;
    an array of light detectors respectively disposed within said array of chambers;
    said chambers configured to enable each of said light detectors to receive diffuse, non-specular reflections of the light from a respective one of the test areas when the sample media is indexed within said holder; and
    said chambers configured to substantially prevent said light detectors from receiving specular reflections of the light.

2. The readhead of claim 1, wherein said light detectors comprise color detectors.

3. The readhead of claim 1, wherein said chambers are configured to substantially prevent said light detectors from receiving specular reflections of the light from the respective one of the test areas.

4. The readhead of claim 1, wherein said chambers are configured to substantially prevent each of said light detectors from receiving reflections from other ones of the test areas.

5. The readhead of claim 1, wherein said housing is adapted for incorporation within the photometric diagnostic instrument.

6. The readhead of claim 1, wherein:
the test areas have substantially planar reflecting surfaces defining a planar direction;
said light sources configured to emit light onto respective ones of the test areas at a predetermined angle of incidence relative to the planar direction;
said light detectors each configured to receive reflections emanating from respective ones of the test areas at predetermined angles of reflectance relative to the planar direction; and
magnitudes of said angles of incidence and said angles of reflection being distinct from one another.

7. The readhead of claim 6, wherein the magnitudes of said angles of incidence and said angles of reflection are sufficiently distinct so that the specular reflections land at least one mm away from channels leading to each chamber.

8. The readhead of claim 7, wherein the angles of incidence are substantially normal to the planar direction and said angles of reflectance are oblique to the planar direction.

9. The readhead of claim 1, wherein the test areas have substantially planar reflecting surfaces defining a planar direction, said array of detectors is offset in the planar direction from said array of sources, and said chambers each include a channel extending towards a respective one of the test areas, so that said channel permits entry of said non-specular reflections while substantially shielding said detectors from said specular reflections.

10. The readhead of claim 1, wherein said light detectors are configured to receive diffuse, non-specular reflections of the light associated with a range of distinct analytes.

11. The readhead of claim 1, wherein the array of light sources comprises an array of devices selected from the group consisting of light emitting diodes (LEDs), VCSELs, tungsten lamps, lightguides, organic LEDs, diode lasers, sunlight, ambient light, or optical fibers.

12. The readhead of claim 11, wherein the array of light sources comprises an array of RGB LEDs.

13. The readhead of claim 1, wherein said array of light detectors comprises an array of CMOS devices.

14. The readhead of claim 1, wherein the chambers comprise shielding configured to shield the light detectors from light entering the chambers from directions other than said angles of reflectance.

15. The readhead of claim 6, comprising a memory device operatively engaged with said light detectors.

16. A miniature photometric diagnostic instrument comprising:
a housing having a hand-held form factor;
said housing including a holder configured for receiving reagent sample media therein, the sample media having a plurality of test areas disposed in spaced relation thereon, each of the test areas configured to react with a sample when disposed in contact with the sample and to change color according to an amount of an analyte in the sample;
the holder sized and shaped for forming an indexed fit with the sample media;
an array of light sources coupled to said housing, each of said light sources configured to emit light onto a respective one of the test areas;
an array of chambers disposed in said housing;
an array of light or color detectors respectively disposed within said array of chambers;
said chambers configured to enable each of said light or color detectors to receive non-specular reflections of the light from a respective one of the test areas when the sample media is indexed within said holder;
said chambers configured to substantially prevent said light or color detectors from receiving specular reflections of the light;
a processor operatively coupled to said light or color detectors and to said light sources; said processor configured to analyze the reflections received by said light or color detectors; and
said processor configured to derive a diagnosis value from said analysis, and to generate an output corresponding thereto.

17. The device of claim 16, wherein said light detectors are configured to receive diffuse, non-specular reflections of the light, said reflections being associated with a range of distinct analytes.

18. The device of claim 16, comprising a memory device coupled to said light or color detector.

19. The device of claim 18, wherein said memory device is configured for storing diagnostic data.

20. The device of claim 19, wherein said memory device is configured for storing calibration data.

21. The device of claim 18, wherein said memory device is configured to store the reflections received by said light or color detectors.

22. The device of claim 16, wherein said diagnosis value comprises the amount of said analyte.

23. The device of claim 16, wherein said diagnosis value comprises a diagnosis of a condition.

24. The device of claim 16, wherein said light or color detector comprises a CMOS device.

25. The device of claim 16, wherein said sample media includes a test strip, and said test areas include test pads.

26. The device of claim 16, wherein said sample media comprises an immuno-assay cassette.

27. The device of claim 16, wherein said sample media comprises a microfluidic device.

28. A method for reading reagent sample media, the sample media having a plurality of test areas disposed in spaced relation thereon, each of the test areas configured to react with a sample when disposed in contact with the sample and to change color according to an amount of an analyte in the sample, the method comprising:
(a) receiving the sample media into a sample holder of a readhead of a photometric diagnostic device, the readhead having a hand-held form factor, and the sample holder configured to maintain the sample media in an indexed fit therewith;
(b) sequentially emitting light onto a respective one of the test areas;
(c) sequentially capturing diffuse, non-specular reflectances of the test areas with respective ones of an array of light or color detectors;
(d) preventing specular reflections of the light from reaching the array of light or color detectors during said sequentially capturing (c);
(e) determining the color of the non-specular reflectances;

(f) deriving the amount of an analyte in the sample from said determining (e); and (g) generating an output signal corresponding to the amount.

29. The method of claim 28, wherein the sample media is selected from the group consisting of test strips, immunoassay cassettes, and microfluidic devices.

30. The method of claim 28, further comprising the step of calibrating the array of light or color detectors.

31. The method of claim 30, wherein said calibrating comprises effecting steps (a)-(e) for a calibration material of known color reflectance.

32. The method of claim 31, wherein said deriving (f) comprises:

dividing the reflectance of the test pad by the reflectance of the calibration material; and multiplying the result of said dividing by the known reflectance of the calibration material to generate a calibrated percent reflectance of the test pad.

33. The method of claim 32, wherein said deriving (f) further comprises comparing the calibrated percent reflectance with known values of amounts of said analyte at various predetermined percent reflectances, to determine the amount of said analyte at said calibrated percent reflectance.

34. A miniature readhead for a photometric diagnostic instrument for illuminating a target area and receiving light from the target area, said readhead comprising:

housing means having a hand-held form factor;

said housing means including holding means for receiving reagent sample media therein, the sample media having a plurality of test areas disposed in spaced relation thereon, each of the test areas configured to react with a sample when disposed in contact with the sample and to change color according to an amount of an analyte in the sample;

the holding means sized and shaped for forming an indexed fit with the sample media;

illumination means coupled to said housing means, for emitting light onto a respective one of the test areas;

chamber means disposed in said housing;

color detection means respectively disposed within said array of chambers;

said chamber means configured to enable each of said light or color detectors to receive diffuse, non-specular reflections of the light from a respective one of the test areas when the sample media is indexed within said holder; and said chamber means configured to substantially prevent said color detection means from receiving specular reflections of the light.

35. A photometric diagnostic instrument comprising:

housing means having a hand-held form factor;

said housing means including holding means for receiving reagent sample media therein, the sample media having a plurality of test areas disposed in spaced relation thereon, each of the test areas configured to react with a sample when disposed in contact with the sample and to change color according to an amount of an analyte in the sample;

the holding means sized and shaped for forming an indexed fit with the sample media;

illumination means coupled to said housing, for emitting light onto a respective one of the test areas;

an array of chamber means;

color detection means respectively disposed within said array of chamber means;

said chamber means configured for enabling said color detection means to receive non-specular reflections of the light from the test areas when the sample media is indexed within said holding means;

said chamber means configured to substantially prevent said color detection means from receiving specular reflections of the light;

processing means operatively coupled to said color detection means and to said illumination means;

said processing means configured to analyze the reflections received by said color detection means; and said processing means configured to derive a diagnosis value from said analysis, and to generate an output corresponding thereto.

* * * * *